United States Patent [19]

James et al.

[11] 4,210,140

[45] Jul. 1, 1980

[54] DEVICE FOR DISPENSING MEDICAMENTS

[75] Inventors: Michael James, Pirton; Paul K. Rand, Hitchin; Gerald W. Hallworth, Ware, all of England

[73] Assignee: Allen & Hanburys Limited, London, England

[21] Appl. No.: 875,884

[22] Filed: Feb. 7, 1978

[30] Foreign Application Priority Data

Feb. 10, 1977 [GB] United Kingdom ................ 5486/77
Feb. 10, 1977 [GB] United Kingdom ................ 5489/77
Apr. 29, 1977 [GB] United Kingdom ............... 18058/77

[51] Int. Cl.² .......................................... A61M 15/00
[52] U.S. Cl. .................................................. 128/266
[58] Field of Search ..................... 128/266, 208, 206

[56] References Cited

U.S. PATENT DOCUMENTS

| | | | |
|---|---|---|---|
| 2,569,720 | 10/1951 | Jesnig | 128/206 |
| 4,013,075 | 3/1977 | Cocozza | 128/208 X |
| 4,098,273 | 7/1978 | Glenn | 128/266 X |
| 4,117,844 | 10/1978 | James | 128/208 X |

Primary Examiner—Henry J. Recla
Attorney, Agent, or Firm—McAulay, Fields, Fisher & Goldstein

[57] ABSTRACT

An inhaler device for administering medicaments contained in capsules of the kind including a capsule body portion fitted with a capsule cap portion. The device has a body shell provided with an internal chamber. An air inlet opening leads into the chamber. An outlet nozzle through which air can be aspirated leads from the chamber. A capsule receptacle is located inside the chamber, and is arranged so that one of said portions of a capsule can be retained therein. A capsule opening means is positioned in the chamber to engage the other said portion of the capsule retained in the capsule receptacle. The receptacle and the opening means being movable with respect to one another to separate the two said capsule portions from each other.

12 Claims, 13 Drawing Figures

DEVICE FOR DISPENSING MEDICAMENTS

BACKGROUND OF THE INVENTION

It is well known to supply medicaments of various kinds in gelatin capsules of cylindrical or "torpedo" form. Many of such capsules are constructed in two parts, one of which (called the capsule body) is partly enclosed within the other (called the capsule cap). The capsules contain a medicament in a powder form. It is common to use such capsules with medicaments for a patient who is expected to inhale the powder through his mouth. For this purpose dispensers are well known which include a mouthpiece through which the patient can inhale and a chamber through which air inhaled by the patient or supplied to the patient can pass to entrain the medicament from a capsule which has been pierced or perforated so that the medicament can pass out of the capsule into the chamber. The present invention seeks to provide an improved inhalation device for such capsules in which the capsule may be separated into its two component parts to enable the medicament to pass out of the capsule.

BRIEF SUMMARY OF THE INVENTION

The invention provides an inhaler device comprising a body shell provided with an internal chamber, at least one air inlet opening leading into the chamber, an outlet nozzle through which air can be aspirated from the chamber, a capsule receptacle inside the chamber, the said receptacle being arranged so that one of said portions of a capsule can be retained therein, and capsule opening means arranged to engage the other said portion of the capsule retained in the capsule receptacle, the receptacle and the opening means being movable with respect to one another to separate the two said capsule portions from each other whereby powdered medicaments can exit from the said capsule portions and be entrained in air flowing through the chamber when air is aspirated through the nozzle.

In one embodiment, the body shell includes two members one of which is slidable within the other so that the body shell can be extended or retracted longitudinally of its axis, a cradle being located in and movable with each of the two members, the two cradles being co-axial with one another and arranged to be in end to end relationship when the two members are retracted and separated when the two members are extended.

In another embodiment, the capsule receptacle is a cradle which is movable inside the chamber to receive, and retain the body portion of a capsule, and wherein the capsule opening means is a plough which is fixed inside the chamber in a position such that the cradle can be moved axially of the chamber past the plough and such that during movement of the cradle in one direction the plough can engage the capsule cap of a capsule retained in the cradle and push it off the capsule body, means being provided for ejecting the capsule body portion from the capsule receptacle after the capsule cap portion has been removed and means being provided to prevent the capsule cap and capsule body portions passing through the nozzle when air is aspirated therethrough.

In another embodiment, an operating member is rotatable with respect to the body shell and is connected with a magazine inside the body shell which magazine has a capsule receptacle extending lengthwise of the body shell but offset from the axis thereof, the said receptacle being arranged to receive a body portion of a capsule the remainder of which projects from the receptacle, and a capsule opening member fixed inside the chamber in a position to engage the projecting portion of a capsule loaded in the receptacle when the rotatable member and magazine are rotated, thereby to separate the projecting portion of the capsule from the portion retained in the receptacle, means for ejecting the retained portion from the receptacle and means for preventing the two capsule portions from passing through the nozzle when air is aspirated therethrough.

In all of the embodiments, the outlet or nozzle is preferably in the form of a mouthpiece, but it can be in a form which makes it capable of insertion in the nostril of a patient.

BRIEF DESCRIPTION OF THE DRAWINGS

Some embodiments of the invention are illustrated in the accompanying drawings in which.

DESCRIPTION OF SOME EMBODIMENTS

Figure 1:
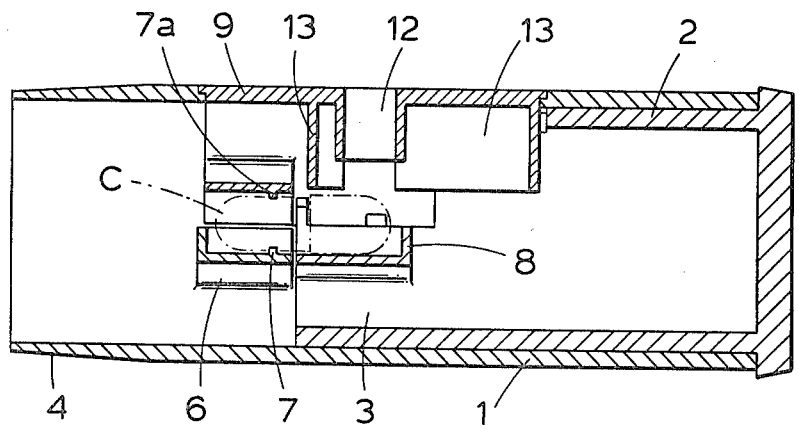
FIG. 1 is a sectional elevation of an inhaler device.
Figure 2:
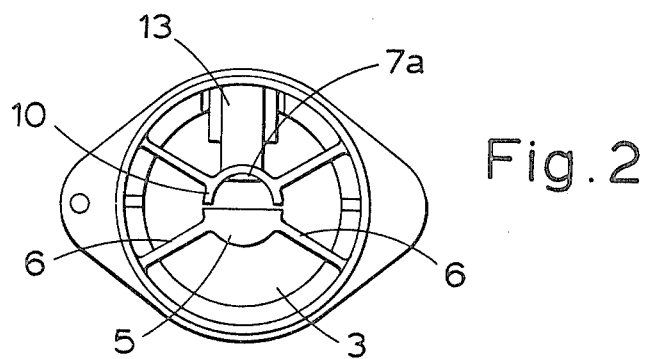
FIG. 2 is an end view.
Figure 3:
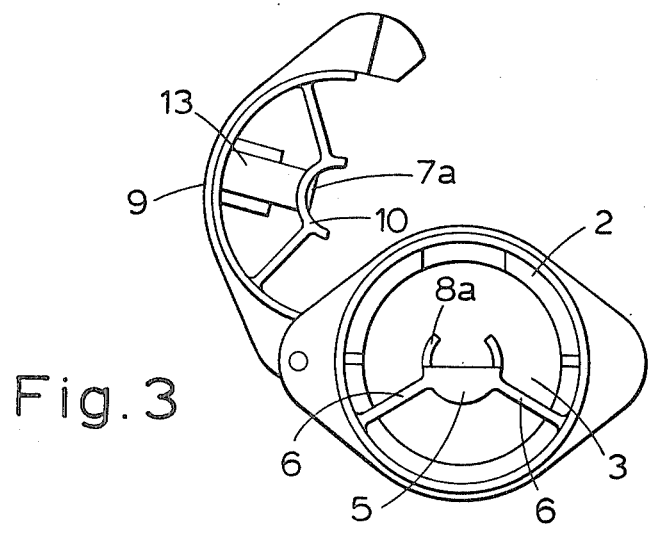
FIG. 3 is an end view similar to FIG. 2, but showing a lid of the device in an open position.
Figure 4:
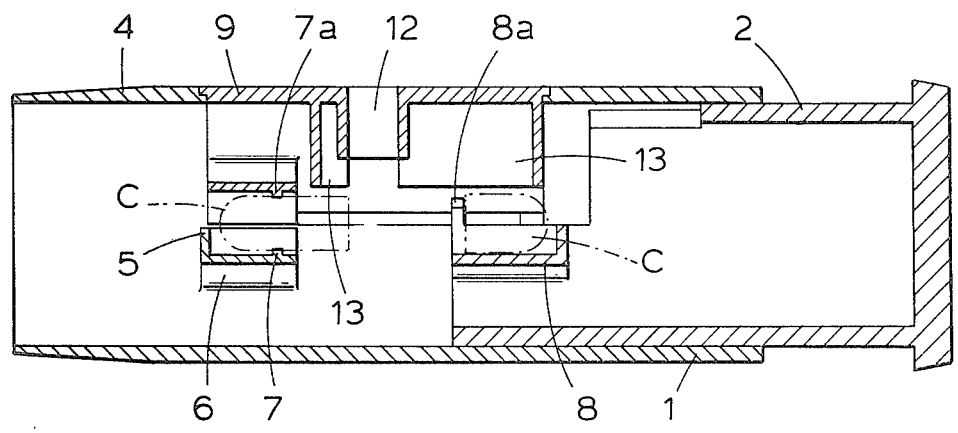
FIG. 4 is a view similar to FIG. 1, but showing the parts in another position.
Figure 5:
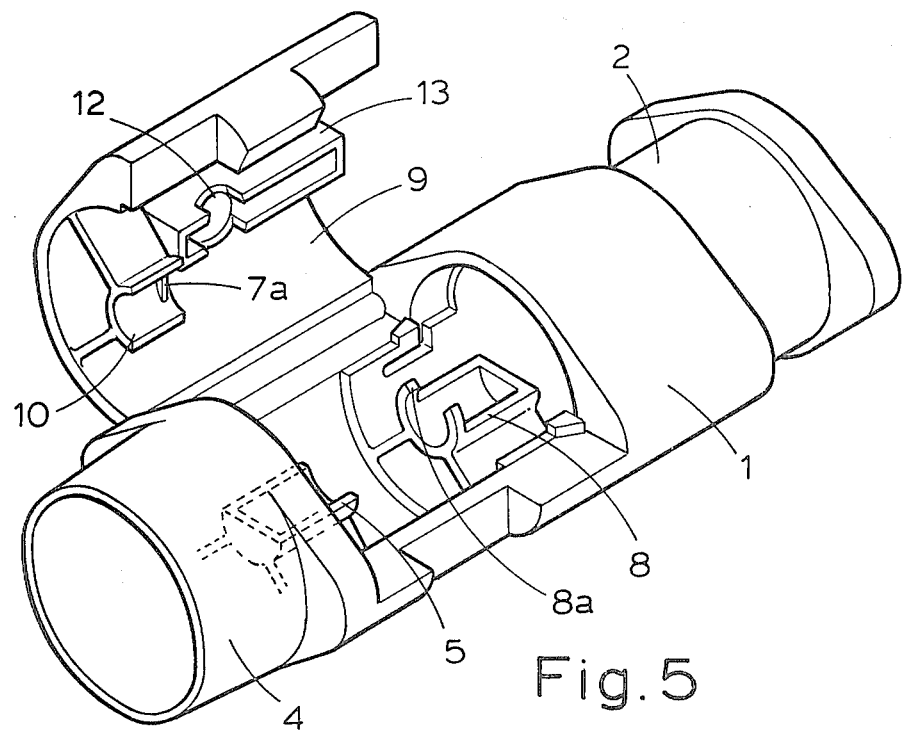
FIG. 5 is a perspective view with the lid in an open position.

In the embodiment of the invention illustrated in FIGS. 1 to 5 an inhaler device from which medicaments can be applied to the mouth of a patient comprises a body of generally elliptical outer cross-section but having a generally cylindrical internal shape. The body is in two parts 1, 2 one of which is slidable within the other so that the body can be extended or retracted longitudinally of its axis. The cylindrical insides of the two parts define an internal chamber 3. One end of the inner or smaller part 2 protrudes from an end of the outer or larger part 1 even when the inner part 2 has been slid into the outer part 1 to its maximum extent. The part 1 has an open end serving as a mouthpiece 4 which can be inserted in the mouth of a patient. For the convenience of description, the mouthpiece 4 of the body is hereinafter considered to be at the forward end of the body.

Arranged inside the part 1 is an axial cradle or capsule receptacle portion 5 on which one end of capsule C can be held. This cradle 5 is supported on arms 6 and includes a clamp tooth 7 which grip a capsule C inserted into the cradle 5. Air flows around and across the capsule. A similar cradle 8 or capsule opening means 8 extends axially in the rear or inner part 2 of the body and is co-axial with the forward cradle 5 so that it can receive the other end of the capsule C. The cradle 8 has an end stop 8a for preventing movement of the capsule cap towards the mouthpiece 4. The outer cylinder 1 is split longitudinally over a portion of its length to form a lid 9 which is hinged to the main portion of the outer cylinder 1. This enables a capsule C to be inserted in or withdrawn from the cradles 5, 8.

The lid 9 of the body has a clamp portion 10 having a clamp tooth 7a and opposed to the cradle 5 which when the lid 9 is closed, moves on to a capsule in the cradle 5 so that the capsule is gripped or clamped. The cradles 5, 8 in the body are movable axially of the dispenser when the body is extended (FIG. 4) so that they will be moved away from each other whereupon the capsule will be divided into two so that the medicament in the capsule can discharge therefrom.

A radial air inlet 12 extends through the lid 9 into the chamber 3. Pressure members 13 are provided in the lid 9 adjacent the air inlet 12 and are arranged to bear on the portion of the capsule C carried by the rear cradle 8.

In use, the lid 9 is opened and a capsule C inserted in the cradles 5, 8 which have been closed together. The capsule cap is located in the cradle 8. The lid 9 is then closed and the portions 1 and 2 of the body drawn apart. The patient then applies the mouthpiece 4 to his mouth and inhales through the mouthpiece. This produces a turbulent flow of air around the capsule body in the cradle 5 sufficient to withdraw powder from the capsule body. The withdrawn powder is entrained and dispersed in the air caused to pass through the body by the inhaling action of the patient and the medicament therefore enters the mouth of the patient. If desired, the cradles 5, 8 parts may be colour-coded or otherwise marked to assist the patient place a similarly marked capsule in the preferred position in the cradles, i.e. with the capsule cap in the cradle 8 and capsule body in the cradle 5.

Figure 6:
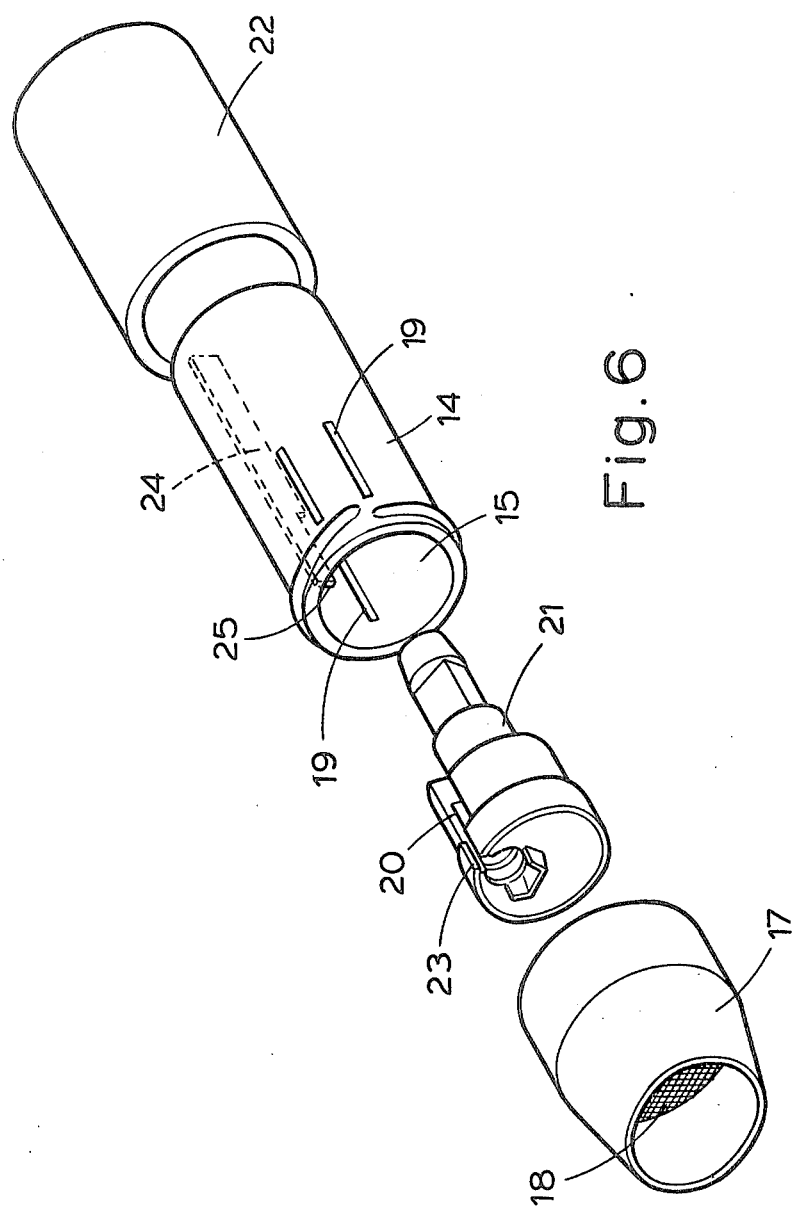
FIG. 6 is an exploded perspective view of another embodiment of the invention.
Figure 7:
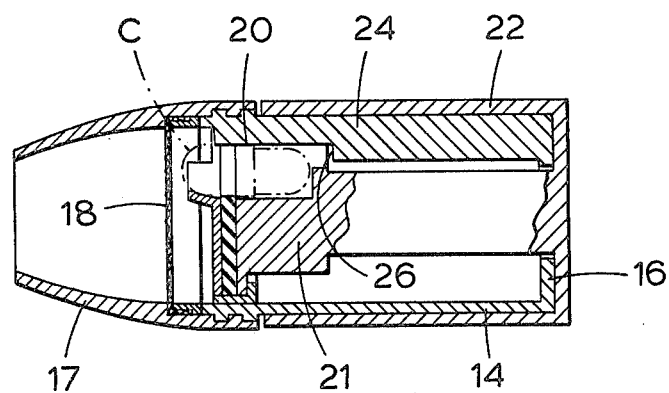
FIGS. 7 and 8 are sectional elevations of the device illustrated in FIG. 6 with parts of the device in two different positions.
Figure 8:
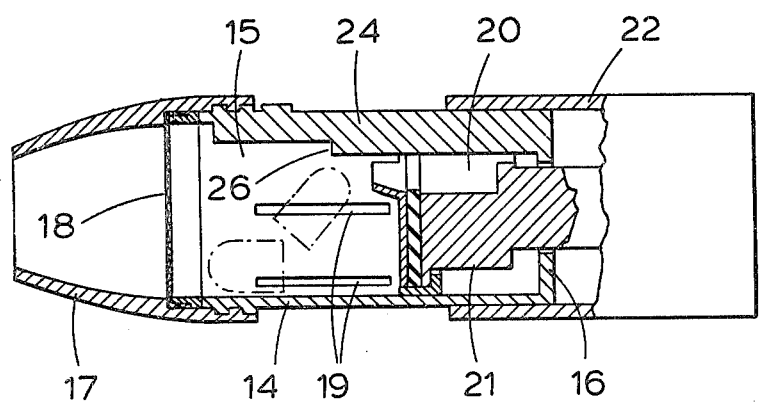
Figure 9:
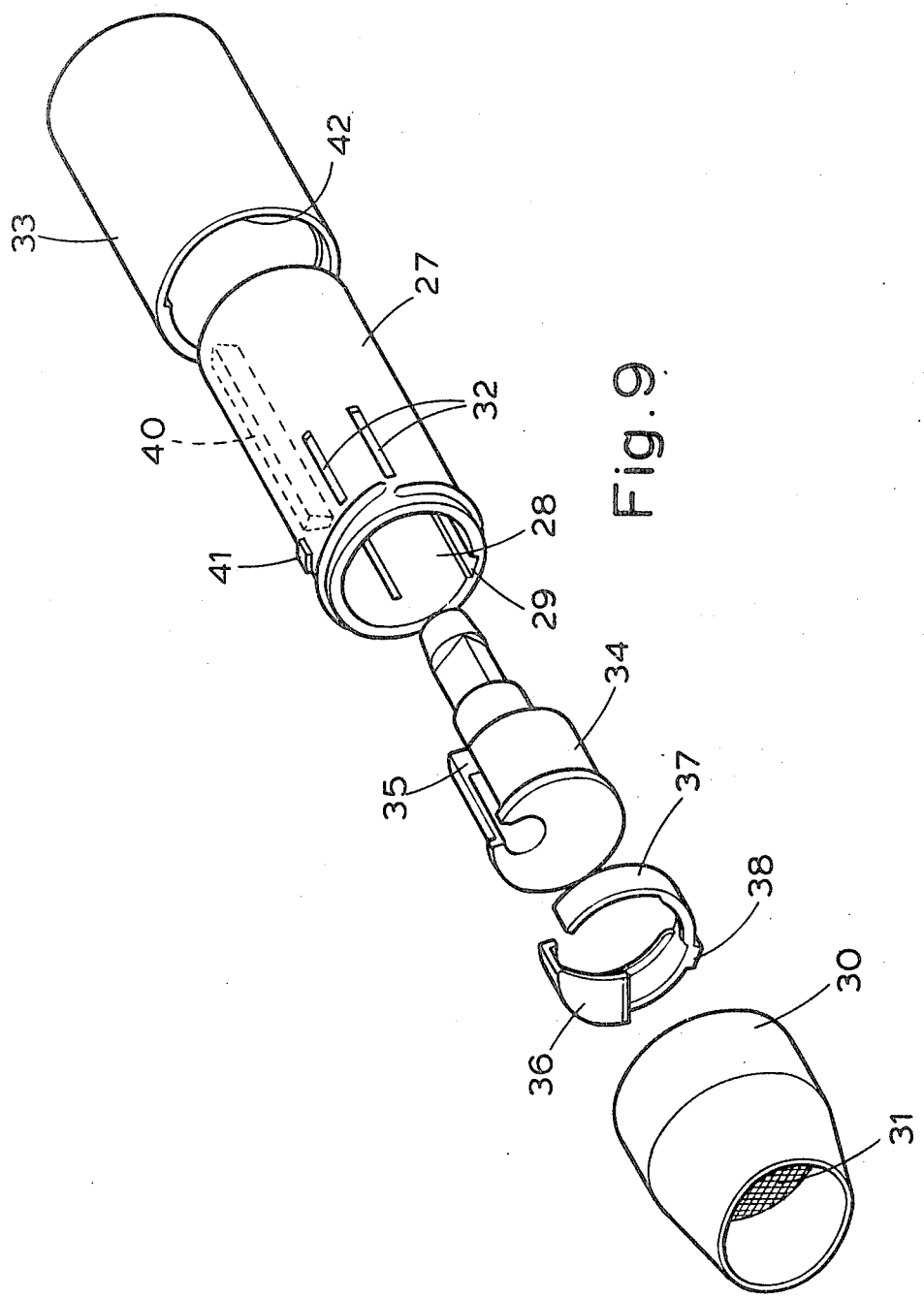
FIG. 9 is an exploded perspective view of another modification.
Figure 10:
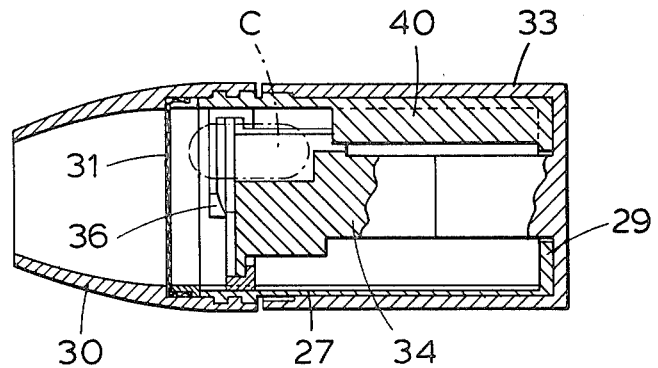
FIG. 10 is a sectional elevation of the device illustrated in FIG. 9, FIGS. 11 and 12 are end views of the device of FIGS. 9 and 10 with mouthpiece removed and showing parts of the device in two different positions.
Figure 11:
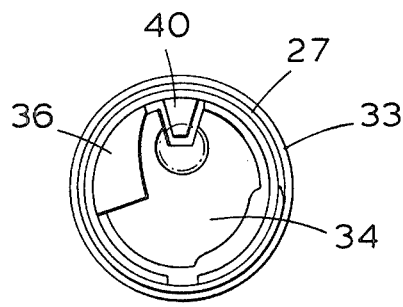
Figure 12:
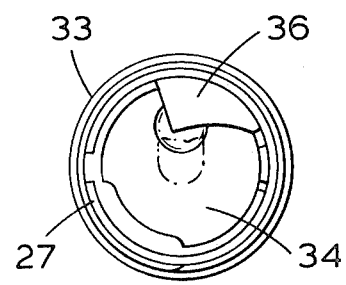
Figure 13:
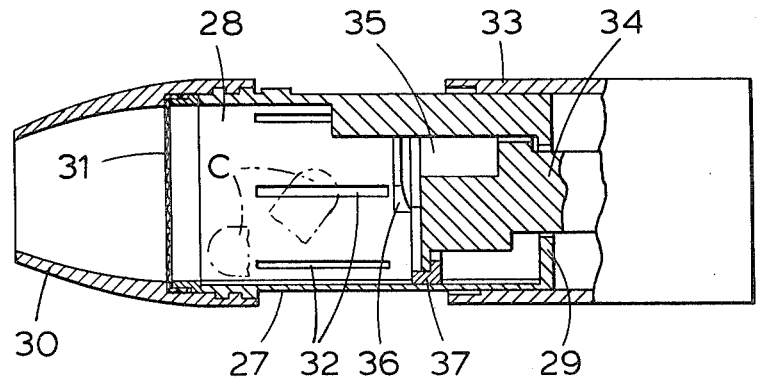
FIG. 13 is a view similar to FIG. 10 but with parts of the device in a different position.

In the embodiment of the invention illustrated in FIGS. 6, 7 and 8, a device according to the invention comprises a hollow cylindrical body 14 the interior of which defines a chamber 15, herein called a dispersion chamber. This body 14 is closed at one end by an end wall 16. A nozzle 17 fits over the other (or front) end of the body. This nozzle is preferably in the form of a mouthpiece which can be inserted in the mouth of a patient, but if desired, the nozzle can be of a size and shape capable of insertion in the nostril of a patient. The nozzle is hereinafter referred to as a mouthpiece.

The dispersion chamber 15 contains a capsule holder or cradle 20 and a capsule opening plough 25 as hereinafter to be described. The mouthpiece 17 is provided with a guard 18 which may be in the form of a perforated sheet of plastics material or of net or gauze which prevents parts of an opened capsule C, but allows medicament from the capsule, to be inhaled through the mouthpiece 17.

The body 14 is provided with a plurality of air inlet slots 19 leading into the dispersion chamber 15. The slots 19 are angled with respect to a diametrical chord of the chamber.

The capsule holder or cradle 20 is located on an axial shaft 21 inside the dispersion chamber 15. This shaft 21 runs through the chamber 15 and out of the rear end wall 16 where it is connected with an operating sleeve 22 surrounding the rear portion of the body 14. The sleeve 22, and therefore the shaft 21 and cradle 20, are axially movable to and from the front end of the dispersion chamber.

The capsule cradle 20 is a receptacle which is basically of cylindrical form and of such a size as to accommodate the capsule body of a capsule C which can be inserted manually therein. The capsule cap portion then projects forwardly of the cradle 20 (see FIG. 7).

The interior of the cradle 20 is arranged tightly to grip the capsule body. It can be of such a size that a standard capsule body is a tight fit in the cradle or it can be provided with suitable ribs or other friction means to provide a firm grip. The cradle has a slot or opening 23 running its full length as clearly shown in FIG. 6.

Fixed inside the dispersion chamber 15, is a capsule opening plough 24 which is conveniently in the form of an internal fin or rib with a plough or hooked end 25 best seen in FIG. 6. The plough 24 is so positioned that when it is moved forwards with the dispersion chamber 15, it is caused to enter the longitudinal opening 23 in the cradle 22.

The shape of the plough is preferably such as to contact as much as possible of the surface area of the capsule C contained in the cradle.

In use, the device is in the closed position illustrated in FIG. 7 and the mouthpiece 17 is removed from the front end of the body 14 and a capsule C is loaded by a patient into the cradle 20. The patient so loads the capsule that the capsule body is inserted in the cradle with the capsule cap projecting from the cradle. The mouthpiece is then replaced and the capsule cradle 20 is then moved backwards inside the chamber. During such movement the plough 24 passes over the capsule C. In so doing it engages the end of the capsule cap and pushes it off the capsule body. The plough 24 conveniently has a portion 26 of suitable size and shape to engage the end of the capsule body after the capsule cap has been removed and puts the capsule body into the dispersion chamber.

When the opened capsule is in the dispersion chamber the patient inhales through the mouthpiece. After the inhalation has been completed, the patient removes the mouthpiece and tips out the spent capsule. The mouthpiece is then replaced after, if desired, having re-loaded the cradle ready for another inhalation operation.

In the embodiment of the invention illustrated in FIGS. 9 to 13, an inhalation device comprises a cylindrical body 27, the interior of which defines a capsule receiving chamber 28. The body 27 is closed at one end by an end wall 29 and is open at the other or front end. A mouthpiece 30 in the form of a removable mouthpiece is screwed or otherwise secured on the front end of the body 27. A grid or guard 31 is provided to prevent the capsule parts, but not the powdered medicament, being withdrawn through the mouthpiece 30 when the patient inhales. This grid or guard 31 is conveniently located at the rear end of the mouthpiece 30. The capsule parts tend to rotate on the grid or guard 31 as the patient inhales.

The central portion of the body 27 has a plurality of air inlet slots 32 running lengthwise of the body 27 as in the previous embodiment. These slots 32 communicate with the chamber 28 and are angled with respect to a diametrical chord of the chamber.

An operating sleeve 33 is telescopically slidable over the rear end portion of the body 27 and is also rotatable thereon. The sleeve 33 is connected with a magazine or barrel portion 34 inside the body so that the sleeve 33 and magazine 34 are slidable and rotatable together as a unit. The magazine has a capsule loading receptacle 35 extending lengthwise of the magazine and body, but offset from the axis of the body and magazine. This loading receptacle 35 is open at the front. A capsule C containing a powdered medicament to be inhaled can be inserted into the open end of the capsule loading receptacle 35 after the mouthpiece 30 has been withdrawn. When the capsule has been inserted in the receptacle 35 a front end portion of the capsule will project from the front of the receptacle 35 (see FIG. 10). When the capsule C has been inserted in the loading receptacle 35 the mouthpiece 30 is replaced.

A wedge-shaped capsule opening member 36 is mounted inside the body within a mounting ring 37. The mounting ring 37 is a sliding fit inside the body 27 and has a key 38 which engages in a keyway 39 inside the body 27. The ring 37 can, therefore, slide with respect to the inside of the body 27 but it cannot rotate. The ring 37 is connected with the front end of the magazine 34 in such a way that the ring can rotate with respect to the magazine but the ring and magazine are slidable together.

A capsule ejector fin 40 is fixed in the body 27 behind the magazine 34 in such an angular position that when the sleeve 33, and therefore the magazine 34, is moved to the open or operative position and the capsule loading receptacle is located with the fin, the fin 40 will enter the loading receptacle 35 (see FIG. 11) thereby to eject the capsule from the open front end of the receptacle 35.

In operation, the device is arranged in the closed position (see FIG. 10) and a capsule containing medicament to be inhaled is loaded into the capsule loading receptacle 35 of the magazine 34 and the mouthpiece 30 is then secured to the body. The sleeve 33 is then rotated by approximately one half turn. Such rotary movement of the sleeve 33 will also rotate the magazine 34 and the capsule C contained in the loading receptacle 35 of the magazine and the capsule opening member 36 and loading receptacle 35 are so positioned with respect to one another that such rotation will engage the projecting portion of the capsule with the forward edge of the opening member. Continued rotation causes the opening member to exert a wedging action on the projecting portion of the capsule. The projecting portion will be separated from the remainder of the capsule as a result of the pressure of this wedging action. The sleeve 33 and magazine 34 are then rotated in the opposite direction back to the original position, and the further wedging action of the member 36 during such rotation will assist in separating the capsule body and cap. Such rotation will also cause the capsule loading receptacle 35, which is open at both ends, to be registered with the capsule ejector fin 40. When the sleeve 33 is correctly positioned, it is slid to its open or operative position and during such movement the fin 40 will enter the capsule loading receptacle 35 of the magazine 34 and in so doing will press against the end of the body of capsule C and push it out of the front end of the loading receptacle into the chamber 28. The patient can then inhale through the mouthpiece 30 so as to inhale the powdered medicament. When the inhalation has been completed the patient can remove the mouthpiece to remove the spent capsule and another capsule can be loaded into the capsule loading receptacle ready for another inhalation.

Means may be provided for positively limiting the relative rotation between the sleeve and the magazine on the one hand and the body on the other. Thus, for example, a stop 41 (FIG. 9) can be provided on the body 27 to run in a recess 42 inside the sleeve 33. The ends of the recess form abutments with which the stop may engage to limit rotation of the sleeve with respect to the body. This arrangement ensures that the fin may be correctly located to eject a capsule part.

What is claimed is:

1. An inhaler device for administering medicaments contained in capsules of the kind including a capsule body portion fitted with a capsule cap portion, the said device comprising a body shell provided with an internal chamber, at least one air inlet opening leading into the chamber, an outlet nozzle through which air can be aspirated from the chamber, a capsule receptacle mounted entirely inside the chamber, the said receptacle including means for retaining one of said portions of a capsule therein, and capsule opening means arranged to engage the other said portion of the capsule retained in the capsule receptacle, the receptacle and the opening means being movable with respect to one another to separate the two said capsule portions from each other whereby powdered medicament can exit from the said capsule portions and be entrained in air flowing through the chamber when air is aspirated through the nozzle.

2. An inhaler device as claimed in claim 1, wherein the capsule receptacle and the capsule opening means is movable apart axially of the chamber thereby to separate one of the said capsule portions from the other.

3. A device as claimed in claim 1, wherein the said capsule receptacle and the said capsule opening means are each cradles arranged inside the chamber to receive and retain one of the said capsule portions, the said cradles being relatively movable between a closed position in which one of the said portions of a capsule can be loaded in each of the cradles and an open position in which they are axially spaced from one another.

4. A device as claimed in claim 3, wherein the body shell includes two members one of which is slidable within the other so that the body shell can be extended or retracted longitudinally of its axis, a cradle being located in and movable with each of the two members, the two cradles being co-axial with one another and arranged to be in end to end relationship when the two members are retracted and separated when the two members are extended.

5. A device as claimed in claim 4, wherein the body shell is split longitudinally over an area surrounding the adjacent ends of the cradles to enable a capsule to be loaded in the cradles when they are in the closed position, the said lid having clamp portions and pressure members engageable with a capsule loaded in the cradles when the lid is closed.

6. An inhaler device as claimed in claim 1, wherein the capsule receptacle is a cradle which is movable inside the chamber to receive and retain the body portion of a capsule and wherein the capsule opening means is a plough which is fixed inside the chamber in a position such that the cradle can be moved axially of the chamber past the plough and such that during movement of the cradle in one direction the plough can engage the capsule cap portion of a capsule retained in the cradle and push it off the capsule body, means being provided for ejecting the capsule body portion from the capsule receptacle after the capsule cap has been removed and, means being provided to prevent the capsule cap and body portions passing through the nozzle when air is aspirated therethrough.

7. An inhaler device as claimed in claim 6, wherein the body shell has thereon an axially movable sleeve, the cradle is located on an axial shaft extending through the chamber and connected with the axially movable sleeve, and the plough is a rib or fin fixed inside the chamber.

8. An inhaler device as claimed in claim 6, wherein the body shell is closed at one end by a nozzle which is removable to permit a capsule to be loaded into the capsule receptacle.

9. An inhaler device as claimed in claim 1, wherein an operating member is rotated with respect to the body shell, and is connected with a magazine inside the body shell which magazine has a capsule receptacle extending lengthwise of the body shell but offset from the axis thereof, the said receptacle being arranged to receive a body portion of a capsule the remainder of which projects from the receptacle, and a capsule opening member fixed inside the chamber in a position to engage the projecting portion of a capsule loaded in the receptacle when rotatable member and magazine are rotated, thereby to separate the projecting portion of the capsule from the portion retained in the receptacle, means for ejecting the retained portion from the receptacle and means for preventing the two capsule portions from passing through the nozzle when air is aspirated therethrough.

10. An inhaler device as claimed in claim 9, wherein the body shell is closed at one end by a nozzle which is removable to permit a capsule to be loaded into the capsule receptacle.

11. An inhaler device as claimed in claim 9, wherein the capsule opening member is a wedge within a mounting ring fixed inside the body shell.

12. An inhaler device as claimed in claim 11, wherein the magazine has a passage extending lengthwise of the body shell but offset from the axis thereof and wherein a capsule ejector fin is fixed inside the body shell in such a position that it can enter either the passage or the capsule receptacle depending on the angular position of the sleeve with respect to the body shell, whereby a portion of a capsule in the capsule receptacle can be ejected from the receptacle as desired.

* * * * *